US010940687B2

(12) United States Patent
Batt et al.

(10) Patent No.: US 10,940,687 B2
(45) Date of Patent: Mar. 9, 2021

(54) SYSTEM AND METHOD FOR LASER INDUCED FORWARD TRANSFER COMPRISING A MICROFLUIDIC CHIP PRINT HEAD WITH A RENEWABLE INTERMEDIATE LAYER

(71) Applicants: Precise Bio Inc, Winston Salem, NC (US); Precise Bio 3D LTD, Hevel Modi'in (IL)

(72) Inventors: Aryeh Batt, Beit Yatir (IL); Amos Eitan, Jerusalem (IL); Ariel Eisenbach, Zufim (IL)

(73) Assignees: Precise Bio Inc, Winston Salem, NC (US); Precise Bio 3D LTD, Hevel Modi'in (IL)

( * ) Notice: Subject to any disclaimer, the term of this patent is extended or adjusted under 35 U.S.C. 154(b) by 0 days.

(21) Appl. No.: 16/605,319

(22) PCT Filed: Apr. 16, 2018

(86) PCT No.: PCT/IL2018/050429
§ 371 (c)(1),
(2) Date: Oct. 15, 2019

(87) PCT Pub. No.: WO2018/193446
PCT Pub. Date: Oct. 25, 2018

(65) Prior Publication Data
US 2020/0070514 A1   Mar. 5, 2020

Related U.S. Application Data

(60) Provisional application No. 62/485,952, filed on Apr. 16, 2017.

(51) Int. Cl.
*B41J 2/14* (2006.01)
*B41M 5/40* (2006.01)
(Continued)

(52) U.S. Cl.
CPC ............ *B41J 2/14104* (2013.01); *B41J 2/045* (2013.01); *B41J 2002/14483* (2013.01);
(Continued)

(58) Field of Classification Search
CPC .................... B41J 2/14104; B41J 2/045; B41J 2002/14483; B41J 2202/12; B41M 5/42; B41M 5/40
See application file for complete search history.

(56) References Cited

U.S. PATENT DOCUMENTS

| 4,531,138 A | * | 7/1985 | Endo | .......................... | B41J 2/14 347/171 |
| 5,521,140 A | * | 5/1996 | Matsuda | .................. | B41J 2/005 347/171 |

(Continued)

FOREIGN PATENT DOCUMENTS

JP     H11105276 A     4/1999

OTHER PUBLICATIONS

Arnold, et al.,"Laser Direct-Write Techniques for Printing of Complex Materials", MRS Bull, 2007, vol. 32, pp. 23-31.
(Continued)

*Primary Examiner* — Yaovi M Ameh
(74) *Attorney, Agent, or Firm* — The Webb Law Firm

(57) ABSTRACT

Methods and systems for Laser-Induced Forward Transfer are disclosed in which a microfluidic chip is used as the printing head. The head comprises a transparent upper region, a middle region comprising an intermediate layer channel and an ink channel in fluid connection with said intermediate layer channel, and a lower layer with an orifice in fluid contact with the ink channel. When material in the intermediate layer channel is irradiated by an energy source (typically a pulsed laser) at a spot opposite the orifice, the material is partially evaporated, creating a vapor bubble that
(Continued)

creates a transient pressure increase when it collapses, thereby forcing ink out of the orifice and onto a receiving substrate.

20 Claims, 4 Drawing Sheets

(51) Int. Cl.
    *B41J 2/045*     (2006.01)
    *B41M 5/42*     (2006.01)

(52) U.S. Cl.
    CPC ............ *B41J 2202/12* (2013.01); *B41M 5/40* (2013.01); *B41M 5/42* (2013.01)

(56) References Cited

U.S. PATENT DOCUMENTS

| | | |
|---|---|---|
| 6,474,783 B1 | 11/2002 | Pilossof et al. |
| 9,446,618 B2 * | 9/2016 | Batt ................ C23C 14/048 |
| 2009/0115820 A1 * | 5/2009 | Nomura ............ B41J 2/14008 347/68 |
| 2016/0296933 A1 | 10/2016 | Chiou et al. |

OTHER PUBLICATIONS

Duocastella, et al., "Time-resolved imaging of the laser forward transfer of liquids", J. Appl. Phys., 2009, vol. 106, 084907, pp. 1-7.

\* cited by examiner

SYSTEM AND METHOD FOR LASER INDUCED FORWARD TRANSFER COMPRISING A MICROFLUIDIC CHIP PRINT HEAD WITH A RENEWABLE INTERMEDIATE LAYER

CROSS-REFERENCE TO RELATED APPLICATIONS

This application is the United States national phase of International Application No. PCT/IL2018/050429 filed Apr. 16, 2018, and claims priority from U.S. Provisional Pat. Appl. No. 62/485,952, filed Apr. 16, 2017, is the disclosures of which are hereby incorporated by reference in their entirety.

FIELD OF THE INVENTION

This invention relates in general to means and methods for Laser Induced Forward Transfer (LIFT). It relates in particular to a microfluidic head for LIFT that incorporates a renewable intermediate layer.

BACKGROUND OF THE INVENTION

Laser Induced Forward Transfer (LIFT) is a printing process, particularly for 3-D printing, that is useful for printing of rigid, highly viscous, or sensitive materials. LIFT methods currently known in the art are of limited efficiency in some uses (particularly for bio-printing) because they tend to require a long preliminary preparation process, complex system design, and materials having a limited shelf life. A general review of the state of the art can be found in the article "Laser Direct-Write Techniques for Printing of Complex Materials" (Arnold, C. B.; Serra, P.; Piqué, A. *MRS Bull.* 32, 2007, 23-31), which is hereby incorporated by reference in its entirety.

The standard LIFT process known in the art is illustrated schematically in FIG. 1. A typical LIFT system 10 comprises a block 100 that delivers material to a receiving substrate 150 upon activation by the output 110 of a pulsed laser (the laser itself is not shown in the figure). Block 100 is suspended in the air above the receiving substrate. Block 100 comprises a substrate 120 that is made of a material that is transparent at the wavelength of the laser output. Substrate 120 is coated with an intermediate layer 130 that is made from a material, typically a metal or polymer, that absorbs strongly at the wavelength of the laser output. A third layer 140 comprising the material to be deposited on the receiving substrate (hereinafter referred to as "ink") coats the intermediate layer, facing the receiving substrate as shown in the illustration. The laser is typically focused on the intermediate layer so that each pulse will deliver its energy to a small spot at the interface between transparent substrate 120 and the intermediate layer.

When the laser is activated, the light pulse delivers energy to a spot on the intermediate layer, creating a bubble of vapor 135. When the bubble of vapor collapses, it generates a transient high pressure in the direction of the ink layer 140, thereby forming a jet of ink 145, which is deposited on a region 155 of the receiving substrate. The relative positions of block 100, laser output 110, and receiving substrate 150 are then adjusted such that each successive laser pulse irradiates fresh intermediate layer, and deposits the ink on a different region of the receiving substrate if so desired. If the ink itself absorbs sufficiently strongly at the wavelength of the laser output, then the ink layer can be coated directly onto the transparent substrate without any need for the intermediate layer.

U.S. Pat. No. 9,446,618 discloses an improved LIFT system and method. In this "Renewable LIFT" system 20, schematically illustrated in FIG. 2, instead of separate ink and intermediate layers, the system utilizes liquid or gel ink 240 contained in a reservoir 260 that has an orifice 265 facing the receiving substrate 250. Inlet 270 allows a constant flow of ink into the reservoir. In Renewable LIFT, laser output 210 is focused via transparent substrate 220 directly into the ink. Vapor bubble 235 is formed within the reservoir and upon collapse produces a pressure spike that forces a jet of ink 245 through the orifice and onto the receiving substrate 250 at location 255. Reservoir inlet 270 permits refilling of the reservoir, or alternatively, a constant flow of ink into and through the reservoir.

While Renewable LIFT allows high throughput and resolution of 10 μm or even less, it also suffers from some drawbacks. Because of mixing, diffusion, and variable flow stability, it is not possible to include an intermediate layer in Renewable LIFT systems. Thus, it is not possible to perform Renewable LIFT using inks that do not absorb strongly at the output wavelength of the laser. Moreover, precise control of the width and flow velocity of the ink layer is difficult, and can vary over time due to such factors as the humidity, atmospheric pressure, etc.

Thus, there remains a long-felt yet unmet need for a LIFT method and system that can overcome these limitations of currently known LIFT systems while maintaining high throughput and high resolution, and that comprises relatively inexpensive components.

SUMMARY OF THE INVENTION

The system disclosed herein is designed to meet this long-felt need. Instead of an arrangement that includes components such as block 100 or reservoir 260, the inventive system and method uses an integrated microfluidic chip (MFC) that controls and stabilizes the flow of ink. The MFC comprises three regions: an upper region comprising material that is substantially transparent at the laser output wavelength; a lower region comprising a small orifice through which droplets of ink are ejected in the direction of a receiving substrate; and a middle region into which two channels are embedded, with a portion of the channels open to each other along their sides over a region opposite the orifice. A fluid that absorbs strongly at the output wavelength of the laser flows through the upper channel, and ink flows through the lower channel. Laser light impinges on the fluid flowing through the upper channel, heating it and thereby leading to the formation of a transient pressure wave that forces ink out of the orifice, similar to the process that occurs in LIFT systems known in the art. The shallowness of the channels decreases the Reynolds number of the flows, thereby maintaining the ink thickness and velocity in front of the orifice by suppressing turbulence within the flow. Due to the small Reynolds numbers and the small size of the channels, the two fluids form uniform layers with stable laminar flow, so that no significant mixing occurs over the region in which the two channels are in contact.

It is therefore an object of the present invention to disclose a Laser-Induced Forward Transfer (LIFT) printing head (400), wherein said LIFT printing head comprises a microfluidic chip (MFC), said MFC comprising three regions:

an upper region (420);
    a middle region (430) comprising at least one ink channel
        (4300) passing through said MFC; at least one intermediate layer channel (4700) passing through said MFC; and a fluid connection (480) within said MFC between said at least one ink channel and said at least intermediate layer channel; and, a lower region (440), said lower region comprising an orifice (465) in fluid connection with said ink channel;

said at least one ink channel and said at least one intermediate layer channel being disposed at said fluid connection (480) such that said ink channel lies between said intermediate layer channel and said orifice.

It is a further object of the present invention to disclose such a LIFT printing head, wherein said orifice opens to a side of said MFC intersected by a line connecting said three regions.

It is a further object of the present invention to disclose a LIFT printing head as defined in any of the above, wherein said orifice opens to a side of said MFC not intersected by a line connecting said three regions.

It is a further object of the present invention to disclose a LIFT printing head as defined in any of the above, wherein said three regions are not disposed vertically one above the other. In some preferred embodiments of the LIFT printing head, said upper region is perpendicular to said orifice.

It is a further object of the present invention to disclose a LIFT printing head as defined in any of the above, wherein at least one of the following is true: (a) said at least one ink channel is characterized by a height of between about 20 µm and about 1 mm and a width of between about 50 µm and about 3 mm; and, (b) said at least one intermediate layer channel is characterized by a height of between about 20 µm and about 1 mm and a width of between about 50 µm and about 3 mm.

It is a further object of the present invention to disclose a LIFT printing head as defined in any of the above, wherein at least one of the following is true: (a) said ink channel is characterized by a height different from that of said intermediate layer channel; and, (b) said ink channel is characterized by a width different from that of said intermediate layer channel.

It is a further object of the present invention to disclose a LIFT printing head as defined in any of the above, wherein said ink channel comprises an ink channel inlet (4301) and an ink channel outlet (4302), said intermediate layer channel comprises an intermediate layer channel inlet (4701) and an intermediate layer channel outlet (4702), and at least one of said channels is characterized by an inlet and an outlet of different areas.

It is a further object of the present invention to disclose a LIFT printing head as defined in any of the above, wherein said MFC is constructed of material selected from the group consisting of PMMA, COC, PDMS, glass, metal, and ceramic. In some preferred embodiments of the LIFT printing head, said MFC is constructed of a rigid polymer comprising glass embedded in said upper region.

It is a further object of this invention to disclose a Laser-Induced Forward Transfer (LIFT) printing system, comprising:

an energy source;

a receiving substrate (450); and, at least one printing head (400) disposed between said energy source and said receiving substrate such that an ink jet created by a pressure transient within said printing head following delivery of a pulse of energy from said energy source to said printing head will exit said printing head toward said receiving substrate, said printing head comprises a microfluidic chip (MFC), said MFC comprising three regions:

an upper region (420);

a middle region (430) comprising at least one ink channel (4300) passing through said MFC, said at least one ink channel comprising an ink channel inlet (4301) and an ink channel outlet (4302); at least one intermediate layer channel (4700) passing through said MFC, said at least one intermediate layer channel comprising an intermediate layer channel inlet (4701) and an intermediate layer channel outlet (4702); and a fluid connection (480) within said MFC between said at least one ink channel and said at least intermediate layer channel; and, a lower region (440), said lower region comprising an orifice (465) in fluid connection with said ink channel;

said at least one ink channel and said at least one intermediate layer channel being disposed at said fluid connection (480) such that said ink channel lies between said intermediate layer channel and said orifice;

an ink reservoir in fluid connection with said ink channel inlet; and, an intermediate layer material reservoir in fluid connection with said intermediate layer channel inlet.

In some embodiments of the LIFT printing system, a line collinear with a center of said output of said energy source passes through said orifice. In some other embodiments of the LIFT printing system, a line collinear with a center of said output of said energy source lies in a plane is perpendicular to a plane containing a line passing through said orifice.

It is a further object of this invention to disclose the LIFT printing system as defined in any of the above, wherein said energy source comprises at least one laser providing pulsed output (410). In some preferred embodiments of the invention, the LIFT printing system comprises focusing means configured to focus said laser output to a spot characterized by a radius of between about 1 µm and about 1 mm.

It is a further object of this invention to disclose the LIFT printing system as defined in any of the above, said energy source comprising at least one laser providing pulsed output (410) and said LIFT printing system comprising intermediate layer material, wherein said laser is configured to provide output at a wavelength at which said intermediate layer material absorbs and of sufficient energy such that upon irradiation by said output, said intermediate layer material is at least partially evaporated.

It is a further object of this invention to disclose the LIFT printing system as defined in any of the above, said energy source comprising at least one laser providing pulsed output (410) and said LIFT printing system comprising intermediate layer material, comprising intermediate layer material, wherein said laser is configured to provide output at a wavelength at which said intermediate layer material absorbs and of sufficient energy such that upon irradiation by said output, said intermediate layer material is at least partially ablated.

It is a further object of this invention to disclose the LIFT printing system as defined in any of the above, said energy source comprising at least one laser providing pulsed output (410) and said LIFT printing system comprising intermediate layer material, wherein said laser is configured to provide output at a wavelength at which said intermediate layer material absorbs and of sufficient energy such that upon irradiation by said output, said intermediate layer material absorbs sufficient energy such that a transient pressure wave is created within said intermediate layer material.

It is a further object of this invention to disclose the LIFT printing system as defined in any of the above, said energy source comprising at least one laser providing pulsed output (410) and said LIFT printing system comprising intermediate layer material, comprising intermediate layer material, wherein said intermediate layer material comprises at least one material selected from the group consisting of dyes and pigments.

It is a further object of this invention to disclose the LIFT printing system as defined in any of the above, said energy source comprising at least one laser providing pulsed output (410) and said LIFT printing system comprising intermediate layer material, comprising intermediate layer material, wherein said intermediate layer material comprises a material selected from the group consisting of food coloring additives, anthocyanin pigments, hemoglobin, β-carotene, melanin, metallic compounds, organometallic compounds, organic compounds, metallic nanoparticles, organometallic nanoparticles, and organic nanoparticles.

It is a further object of this invention to disclose the LIFT printing system as defined in any of the above, said energy source comprising at least one laser providing pulsed output (410) and said LIFT printing system comprising intermediate layer material, comprising focusing means for focusing said pulsed output at a location selected from the group consisting of an interface between said at least one ink channel and said upper region and within said ink channel.

It is a further object of this invention to disclose the LIFT printing system as defined in any of the above, said energy source comprising at least one laser providing pulsed output (410) and said LIFT printing system comprising intermediate layer material, comprising at least one optical fiber disposed so as to transmit said pulsed output from said laser to said printing head. In some preferred embodiments of the invention, said optical fiber is inserted into said MFC and immersed in said ink. In some other preferred embodiments of the invention, said optical fiber is kept outside of the MFC, and said system comprises collimating and focusing means configured to collimate light emitted from said optical fiber to refocus said light into said MFC. In yet other preferred embodiments of the invention, it comprises comprising a focuser embedded at an end of said optical fiber and configured to focus light emitted from said end of said optical fiber to a predetermined location. In some preferred embodiments of the invention, said optical fiber is selected from the group consisting of hollow-core optical fibers and photonic-crystal fibers (PCFs).

It is a further object of this invention to disclose the LIFT printing system as defined in any of the above, wherein said three regions are disposed substantially vertically one above the other, and said orifice opens to a side of said MFC intersected by a line connecting said three regions.

It is a further object of this invention to disclose the LIFT printing system as defined in any of the above, wherein said three regions are disposed substantially vertically one above the other, and said orifice opens to a side of said MFC not intersected by a line connecting said three regions.

It is a further object of this invention to disclose the LIFT printing system as defined in any of the above, wherein at least one of the following is true: (a) said at least one ink channel is characterized by a height of between about 20 μm and about 1 mm and a width of between about 50 μm and about 3 mm; and, (b) said at least one intermediate layer channel is characterized by a height of between about 20 μm and about 1 mm and a width of between about 50 μm and about 3 mm.

It is a further object of this invention to disclose the LIFT printing system as defined in any of the above, wherein at least one of said channels is characterized by an inlet and an outlet of different areas.

It is a further object of this invention to disclose the LIFT printing system as defined in any of the above, wherein said MFC is constructed of material selected from the group consisting of PMMA, COC, PDMS, glass, metal, and ceramic. In some preferred embodiments of the invention, said MFC is constructed of a polymer and comprising glass embedded in said upper region.

It is a further object of this invention to disclose the LIFT printing system as defined in any of the above, comprising at least one of: (a) pumping means for pumping ink from said ink reservoir to said ink channel inlet and through said ink channel; and, (b) pumping means for pumping intermediate layer material from said intermediate layer reservoir to said intermediate layer channel inlet and through said intermediate layer channel.

It is a further object of this invention to disclose the LIFT printing system as defined in any of the above, wherein at least one of the following is true: (a) said ink channel outlet is in fluid communication with said ink reservoir; and, (b) said intermediate layer channel outlet is in fluid communication with said intermediate layer material reservoir. In some preferred embodiments of the invention, the LIFT printing system comprises at least one of: (a) pumping means for recirculating ink from said ink reservoir through said ink channel inlet and back to said ink reservoir; and, (b) pumping means for recirculating intermediate layer material from said intermediate layer reservoir through said intermediate layer channel and back to said intermediate material reservoir.

It is a further object of this invention to disclose the LIFT printing system as defined in any of the above, wherein one of the following is true: (a) at least one of said head and said receiving substrate is mounted on an XYZ stage having a precision of ±1 μm or better in each direction, and (b) one of said head and said receiving substrate is mounted on an XY stage having a precision of ±1 μm or better in each direction, and the other component is mounted on a stage or mount configured to move said other component along a Z axis.

It is a further object of this invention to disclose the LIFT printing system as defined in any of the above, comprising n printing heads, n>1. In some preferred embodiments of the invention, said energy source is configured to irradiate each of said n printing heads sequentially. In some preferred embodiments of the invention in which the LIFT printing system comprises a plurality of n energy sources, each of the energy sources is configured to irradiate one of said n printing heads.

It is a further object of this invention to disclose the LIFT printing system as defined in any of the above, wherein said head is located above said receiving substrate.

It is a further object of this invention to disclose the LIFT printing system as defined in any of the above, wherein said head is located below said receiving substrate.

It is a further object of this invention to disclose the LIFT printing system as defined in any of the above, wherein said head is located alongside said receiving substrate.

It is a further object of this invention to disclose the LIFT printing system as defined in any of the above, wherein said system is in a location characterized by an environment, said system comprising environmental control means configured to control at least one environmental parameter of said environment. In some preferred embodiments of the invention, said at least one environmental parameter is selected from the group consisting of temperature, humidity, $CO_2$ concentration, and $O_2$ concentration.

It is a further object of this invention to disclose the LIFT printing system as defined in any of the above, wherein said MFC is separated from said receiving substrate by a distance of between about 50 μm and about a few mm.

It is a further object of this invention to disclose a method for Laser-Induced Forward Transfer (LIFT) printing, wherein said method comprises:
  obtaining a LIFT printing system comprising:
    an energy source;
    a receiving substrate (450); and,
    at least one printing head (400) disposed between said energy source and said receiving substrate such that an ink jet created by a pressure transient within said printing head following delivery of a pulse of energy from said energy source to said printing head will exit said printing head toward said receiving substrate, said printing head comprises a microfluidic chip (MFC), said MFC comprising three regions:
      an upper region (420);
      a middle region (430) comprising at least one ink channel (4300) passing through said MFC, said at least one ink channel comprising an ink channel inlet (4301) and an ink channel outlet (4302); at least one intermediate layer channel (4700) passing through said MFC, said at least one intermediate layer channel comprising an intermediate layer channel inlet (4701) and an intermediate layer channel outlet (4702); and, a fluid connection (480) within said MFC between said at least one ink channel and said at least intermediate layer channel; and,
      a lower region (440), said lower region comprising an orifice (465) in fluid connection with said ink channel; said at least one ink channel and said at least one intermediate layer channel being disposed at said fluid connection (480) such that said ink channel lies between said intermediate layer channel and said orifice;
    an ink reservoir in fluid connection with said ink channel inlet; and,
    an intermediate layer material reservoir in fluid connection with said intermediate layer channel inlet;
  flowing ink from said ink reservoir through said at least one ink channel (4300);
  flowing intermediate layer material from said intermediate layer reservoir through said at least one intermediate layer channel (4700);
  irradiating said intermediate layer material with output (410) of an energy source, said output having sufficient energy at a location at which said intermediate layer material is irradiated to at least partially evaporate said intermediate layer material at said fluid connection (480), such that upon collapse of a vapor bubble formed upon said irradiation, a transient pressure increase is created, thereby forcing ink out of said orifice; and,
  receiving said ink forced out of said orifice on at least one predetermined location (455) on a receiving substrate (450).

In some preferred embodiments of the method, said step of flowing ink comprises flowing said ink at a flow rate of between about 1 mm s$^{-1}$ and about 1 m s$^{-1}$. In some preferred embodiments of the method, said step of flowing ink comprises flowing said ink at a volumetric flow rate of less than 0.01 μL s$^{-1}$.

It is a further object of this invention to disclose the method as defined in any of the above, wherein said step of flowing intermediate layer material comprises flowing said intermediate layer material at a flow rate of between about 1 mm s$^{-1}$ and about 1 m s$^{-1}$.

It is a further object of this invention to disclose the method as defined in any of the above, wherein said step of flowing intermediate layer material comprises flowing said intermediate layer material at a volumetric flow rate of less than 0.01 μL s$^{-1}$.

It is a further object of this invention to disclose the method as defined in any of the above, wherein said upper region is substantially transparent to said energy output.

It is a further object of this invention to disclose the method as defined in any of the above, wherein said step of irradiating comprises irradiating with output of a pulsed laser at a wavelength at which said intermediate material absorbs.

It is a further object of this invention to disclose the method as defined in any of the above, wherein said intermediate layer material comprises a material selected from the group consisting of food coloring additives, anthocyanin pigments, hemoglobin, β-carotene, melanin, metallic compounds, organometallic compounds, organic compounds, metallic nanoparticles, organometallic nanoparticles, and organic nanoparticles.

It is a further object of this invention to disclose the method as defined in any of the above, comprising focusing said output at a location selected from the group consisting of an interface between said at least one intermediate layer channel and said upper region and within said intermediate layer channel. In some preferred embodiments of the invention, said step of focusing comprises focusing said output to a spot characterized by a radius of between about 1 μm and about 1 mm.

It is a further object of this invention to disclose the method as defined in any of the above wherein said step of irradiating comprises irradiating with the output of a pulsed laser, and said step of irradiating comprises transmitting said pulsed output from said laser to said printing head by means of an optical fiber. In some preferred embodiments of the method, said optical fiber is inserted into said MFC and immersed in said intermediate layer material. In some preferred embodiments of the method, said optical fiber is kept outside of the MFC, said method comprising collimating and focusing light emitted from said optical fiber. In some preferred embodiments of the method, it comprises focusing light emitted from said end of said optical fiber to a predetermined location by means of a focuser embedded at an end of said optical fiber from which light is emitted. In some preferred embodiments of the invention, said optical fiber is selected from the group consisting of hollow-core optical fibers and photonic-crystal fibers (PCFs).

It is a further object of this invention to disclose the method as defined in any of the above, wherein said three regions are disposed substantially vertically one above the other, and said orifice opens to a side of said MFC intersected by a line connecting said three regions.

It is a further object of this invention to disclose the method as defined in any of the above, wherein said three regions are disposed substantially vertically one above the other, and said orifice opens to a side of said MFC not intersected by a line connecting said three regions.

It is a further object of this invention to disclose the method as defined in any of the above, wherein said step of flowing ink from said ink reservoir through said at least one ink channel comprises pumping said ink from said ink reservoir to said ink channel inlet and through said ink channel.

It is a further object of this invention to disclose the method as defined in any of the above, wherein said step of flowing intermediate layer material from said intermediate layer reservoir through said at least one intermediate layer channel comprises pumping said intermediate layer material from said intermediate layer material reservoir to said intermediate layer material channel inlet and through said intermediate layer material channel.

It is a further object of this invention to disclose the method as defined in any of the above, wherein said step of flowing ink from said ink reservoir through said at least one ink channel comprises recirculating said ink back into said ink reservoir.

It is a further object of this invention to disclose the method as defined in any of the above, wherein said step of flowing intermediate layer material from said intermediate layer material reservoir through said at least one intermediate layer channel comprises recirculating said intermediate layer material back into said intermediate layer material reservoir.

It is a further object of this invention to disclose the method as defined in any of the above, wherein said step of flowing ink through at said least one ink channel comprises flowing ink through at least one ink channel characterized by a height of between about 20 μm and about 1 mm and a width of between about 50 μm and about 3 mm.

It is a further object of this invention to disclose the method as defined in any of the above, wherein said step of flowing intermediate layer material through at said least one intermediate layer material channel comprises flowing intermediate layer material through at least one intermediate layer material channel characterized by a height of between about 20 μm and about 1 mm and a width of between about 50 μm and about 3 mm.

It is a further object of this invention to disclose the method as defined in any of the above, wherein at least one channel is characterized by an inlet and an outlet of different areas.

It is a further object of this invention to disclose the method as defined in any of the above, wherein said MFC is constructed of material selected from the group consisting of PMMA, COC, PDMS, glass, metal, and ceramic. In some preferred embodiments of the invention, said MFC is constructed of a polymer and comprising glass embedded in said upper region.

It is a further object of this invention to disclose the method as defined in any of the above, comprising a step selected from: (a) positioning at least one of said head and said receiving substrate on an XYZ stage having a precision of ±1 μm or better in each direction; and (b) positioning at least one of said head and said receiving substrate on an XY stage having a precision of ±1 μm or better in each direction, and the other component on a stage or mount configured to move said other component along a Z axis.

It is a further object of this invention to disclose the method as defined in any of the above, comprising recirculating said ink via a reservoir in fluid connection with said inlet and with said outlet.

It is a further object of this invention to disclose the method as defined in any of the above, wherein said step of flowing comprises flowing said ink through channels in n printing heads, n>1, and said step of irradiating comprises irradiating ink in each of said n printing heads. In some preferred embodiments of the invention, said step of irradiating comprises irradiating each of said n printing heads sequentially. In some preferred embodiments of the invention, said step of irradiating comprises irradiating with the output of n energy sources, each of which is configured to irradiate one of said n printing heads.

It is a further object of this invention to disclose the method as defined in any of the above, wherein said printing head is located above said receiving substrate.

It is a further object of this invention to disclose the method as defined in any of the above, wherein said printing head is located below said receiving substrate.

It is a further object of this invention to disclose the method as defined in any of the above, wherein said printing head is located alongside said receiving substrate.

It is a further object of this invention to disclose the method as defined in any of the above, comprising moving said printing head relative to said substrate during said LIFT printing process.

It is a further object of this invention to disclose the method as defined in any of the above, wherein said system is in a location characterized by an environment, said method comprising controlling at least one environmental parameter of said environment. In some preferred embodiments of the invention, said step of controlling at least one environmental parameter comprises controlling at least one environmental parameter selected from the group consisting of temperature, humidity, $CO_2$ concentration, and $O_2$ concentration.

It is a further object of this invention to disclose the method as defined in any of the above, wherein said step of irradiating is performed repeatedly at a repetition rate of at least 1 Hz.

BRIEF DESCRIPTION OF THE DRAWINGS

The invention will now be described with reference to the drawings, wherein.

DETAILED DESCRIPTION OF THE PREFERRED EMBODIMENTS

Figure 1:
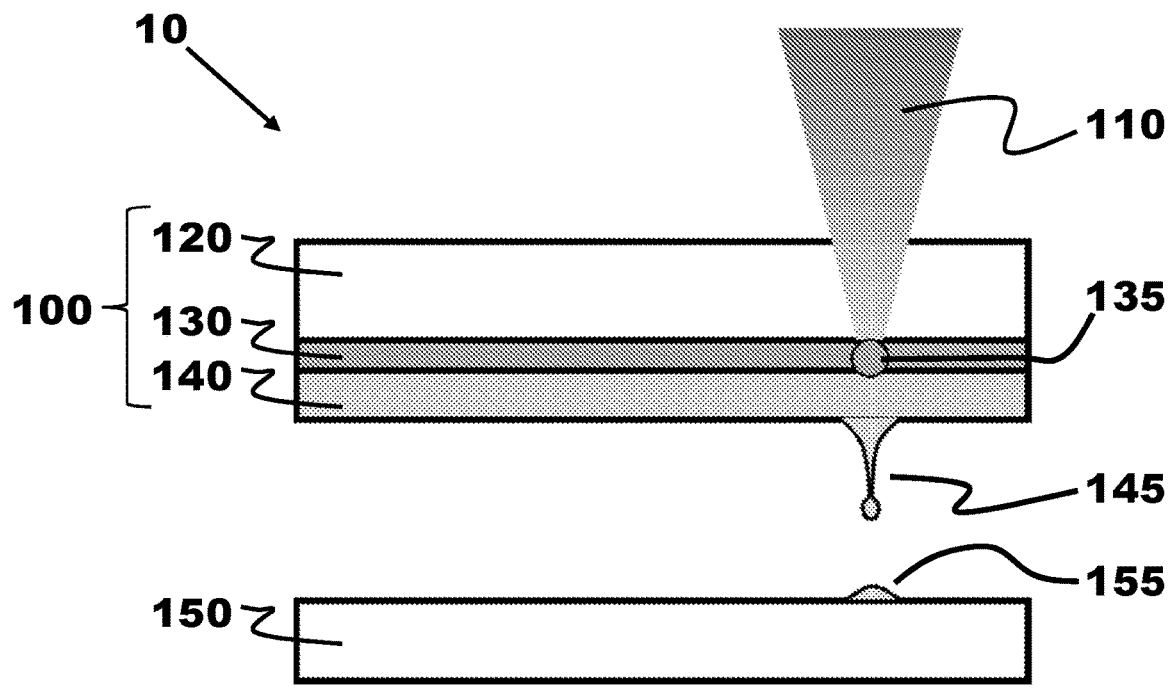
FIG. 1 illustrates schematically the principles of LIFT as known in the art.
Figure 2:
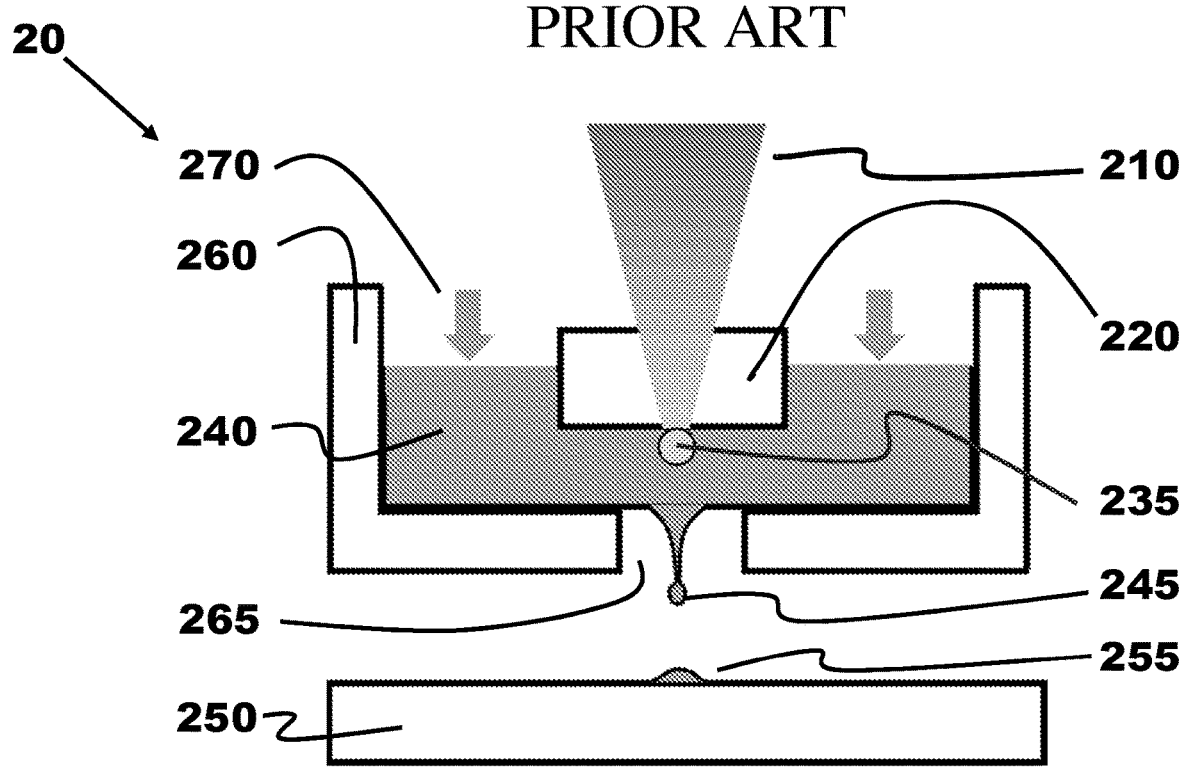
FIG. 2 illustrates schematically a second type of LIFT system known in the art; and, FIG. 3 illustrates schematically one embodiment of a LIFT system of the present invention that incorporates a microfluidic chip with a renewable intermediate layer as a LIFT head, with FIG. 3A showing a schematic cross-sectional view and FIG. 3B showing a schematic three-dimensional view illustrating the flow of ink through the microfluidic chip.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof.

As used herein, the abbreviation "LIFT" stands for "Laser Induced Forward Transfer."

As used herein, the abbreviation "MFC" stands for "microfluidic chip."

As used herein, the abbreviation "PMMA" stands for "poly(methyl methacrylate)."

As used herein, the abbreviation "COC" "cyclic olefin copolymer."

As used herein, the abbreviation "PDMS" stands for "polydimethylsiloxane."

As used herein, the term "ink" refers to any substance that is deposited from the MFC head onto a receiving substrate.

As used herein, with reference to LIFT printing technology, the term "ink jet" refers to ink expelled from a LIFT device to be deposited on a substrate. The "jet" may comprise a stream of ink or one or more droplets.

As used herein, with reference to numerical quantities the term "about" refers to a value within a range of ±25% of the nominal quantity.

In addition, in the following description of the geometry of the MFC print head, the terms "upper," "middle," and "lower" are used to describe three regions into which the MFC is divided. The terms do not necessarily refer to the absolute physical locations of the regions in space, but rather are used for simplicity and convenience to describe the general construction of the MFC. In this context, the term "upper" refers to that region of the MFC through which energy is transferred from an energy source to ink located in an ink channel inside the MFC; the term "lower" refers to that region of the MFC that contains an orifice from which ink is expelled from the MFC head towards a receiving substrate; and the term "middle" refers to that region of the MFC that contains a channel through which ink flows during the LIFT process. While in some embodiments of the invention, the regions are disposed generally vertically one above the other, the terms are not to be construed to limit the construction of the MFC to any specific geometric arrangement of the three regions.

In the following description of the LIFT system of the present invention, for simplicity, embodiments of the system and method are described in which the output of a pulsed laser is used as the energy source for creating the jet of ink that is sent to the receiving substrate. Since the general principle of LIFT requires only the formation of a pressure transient rather requiring that the pressure transient be caused specifically as a result of absorption of energy emanating from a laser, any method for creating an energy pulse sufficiently strong to cause the creation of an ink jet via forward transfer of energy is considered by the inventors to be within the scope of the invention. Non-limiting examples of energy sources other than pulsed lasers that can be used in the present invention include electric arcs, flashlamps, and ultrasonic resonators.

Figure 3A:
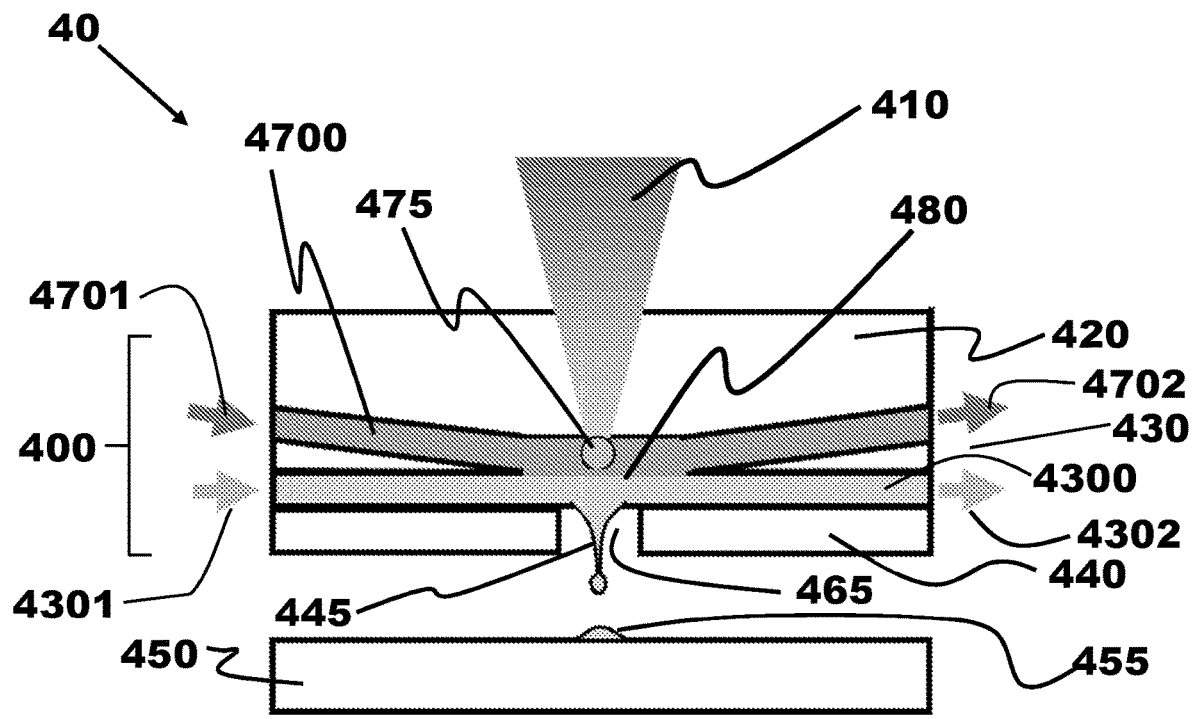
Figure 3B:
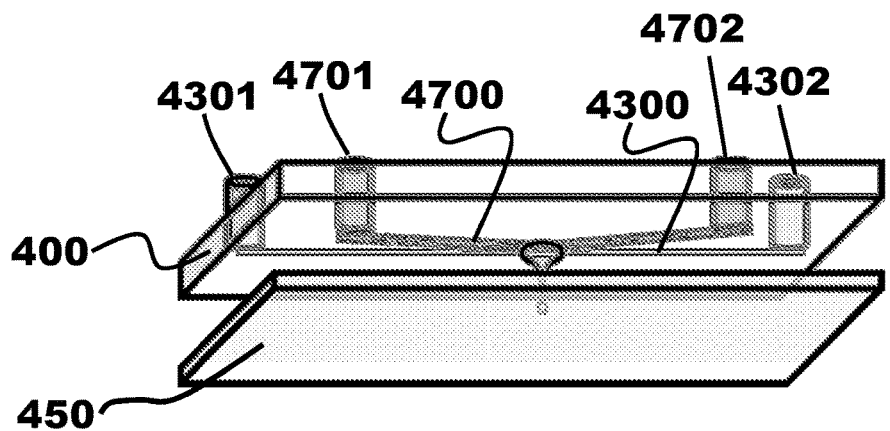

Reference is now made to FIG. 3, which presents a schematic diagram of a typical non-limiting embodiment 40 of a LIFT system that includes a microfluidic chip LIFT head of the present invention. A cross-sectional view is shown in FIG. 3A, while FIG. 3B shows a view from beneath the LIFT head that illustrates the inlet and outlet connections of the fluid flow channels of the MFC LIFT head. The system comprises an MFC 400, which serves as the LIFT head, and a receiving substrate 450 onto which ink is deposited from the LIFT head. The MFC comprises three regions: (1) a relatively thick upper region 420; (2) a relatively thin middle region 430 comprising at least two channels that pass through the body of the MFC: an intermediate layer channel 4700 and an ink channel 4300, which is disposed further from the upper region than is intermediate layer channel 4700; and (3) a relatively thin lower region 440 that includes an orifice 465 facing the receiving substrate.

A fluid connection 480 between is provided between the two channels within the MFC. In preferred embodiments, the fluid connection is opposite orifice 465, that is, the fluid connection is positioned such that a line connecting the center of orifice 465 and the area over which the energy source enters the upper region of the MFC (e.g. the center of the laser beam) will pass through the fluid connection.

In the embodiment of the MFC LIFT head illustrated schematically in FIG. 3, the two channels are curved and are linked to each other opposite the orifice. A gap in walls of the channels in this area of linkage provides the fluid connection between them.

Figure 4:
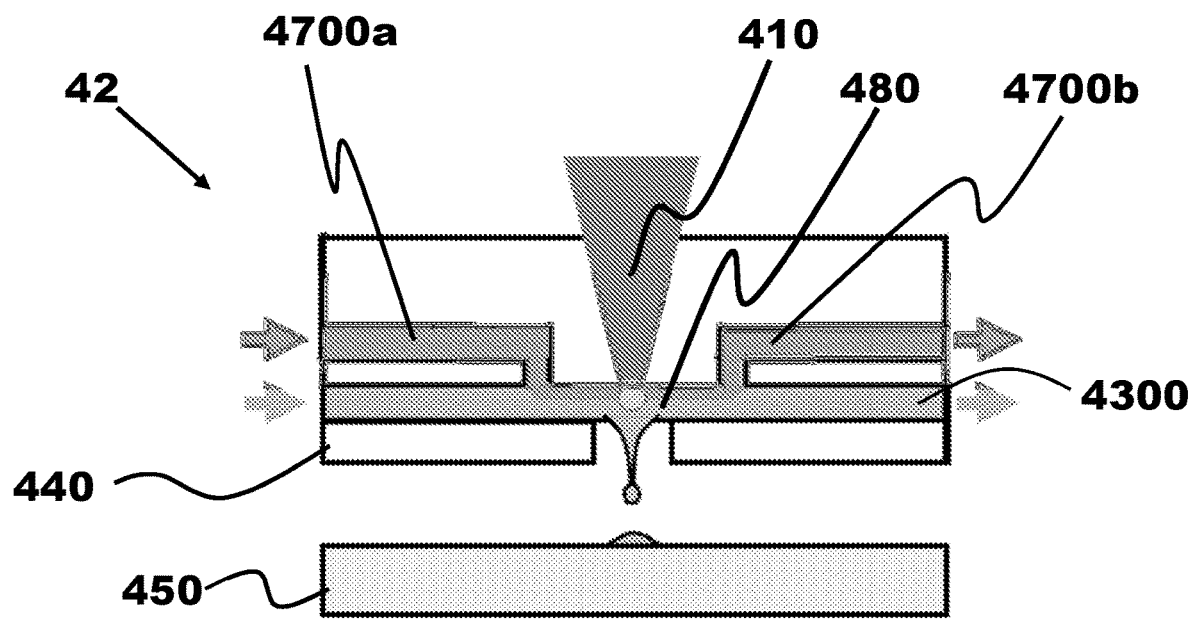
FIG. 4 illustrates schematically a second embodiment of a LIFT system of the present invention.

Reference is now made to FIG. 4, which presents a schematic illustration of a second non-limiting embodiment 42 of the system of the present invention. In the embodiment shown in the figure, the intermediate layer channel is divided into two portions, 4700a and 4700b, the interior end of each of which connects to the ink channel within the MFC. In this embodiment, fluid connection 480 is provided by the two connections between the intermediate layer and ink channels.

The MFC can be made of any appropriate material. The following non-limiting examples of materials of construction are given to assist the person of ordinary skill in the art how to make and use the invention disclosed herein; no limitations on physical or chemical properties such as rigidity or elasticity of materials suitable for use in the MFC are to be inferred from the following discussion. Typical materials of construction include polymers such as poly(methyl methacrlyate) (PMMA), cyclic olefin copolymer (COC), and polydimethylsiloxane (PDMS), as well as materials such as glass, metal, ceramic, etc. In some embodiments of the invention, the MFC is made of a polymer such as PMMA, and glass is embedded in the upper region (described in detail below) in order to prevent damage to the chip by the high temperatures and pressures that are developed during the LIFT process. In some other embodiments of the invention, the MFC is made of a polymer such as PDMS bonded to a glass slide, according to methods that are well-known in the art.

Upper region 420 is constructed of a material that will allow the energy that drives the LIFT process to pass through to the intermediate layer channel. For example, when a laser is used as the energy source, upper region 420 is sufficiently transparent to laser output 410 to permit enough light to pass through the upper region such that light impinging on the intermediate layer retains enough energy to evaporate enough of the material in the intermediate layer to produce a vapor bubble 475 that will, upon collapse, provide a pressure transient sufficiently great to force ink out of the orifice in the direction of the receiving substrate.

Figure 5:
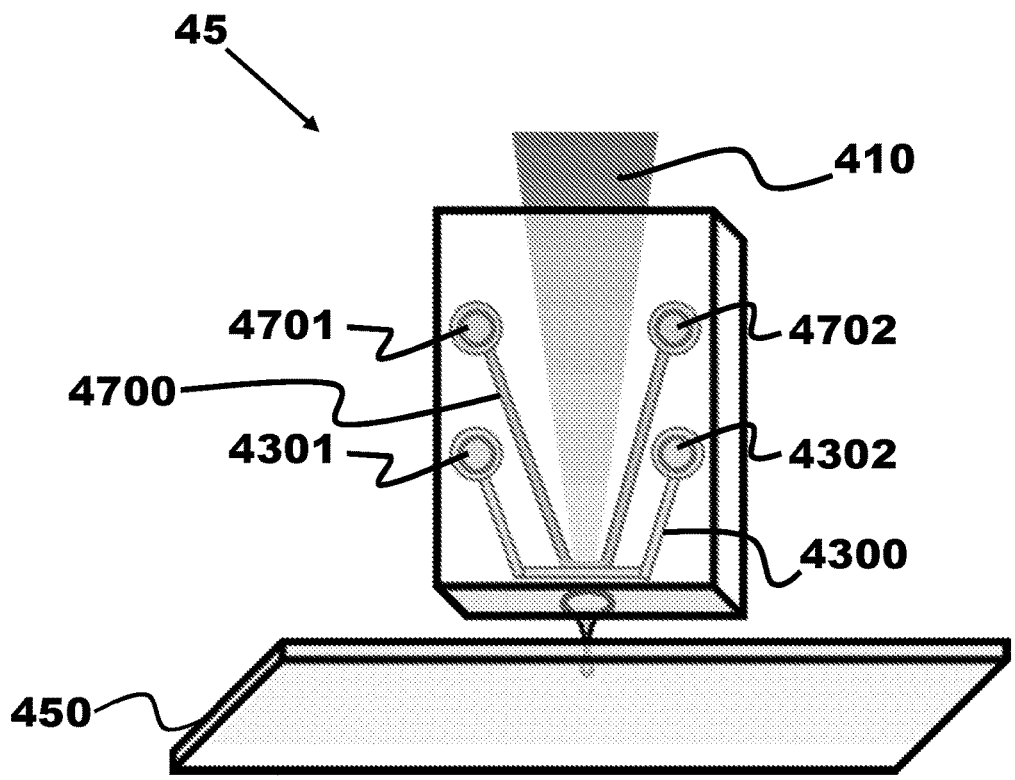
FIG. 5 illustrates schematically a portion of a third embodiment of a LIFT system of the present invention in which ink jet ejection occurs from the narrow side of the microfluidic chip; and, FIGS. 6A and 6B illustrate schematically bottom and side views of a fourth embodiment of a LIFT system of the present invention in which ink jet ejection occurs perpendicular to the direction of propagation of the laser light beam that acts as the LIFT energy source.

Reference is now made to FIG. 5, which presents schematically a third non-limiting embodiment 45 of the LIFT head of the instant invention. In this embodiment, the ink jet is emitted from the narrow side of the MFC rather than from the broad side as shown in FIGS. 3 and 4.

Figure 6A:
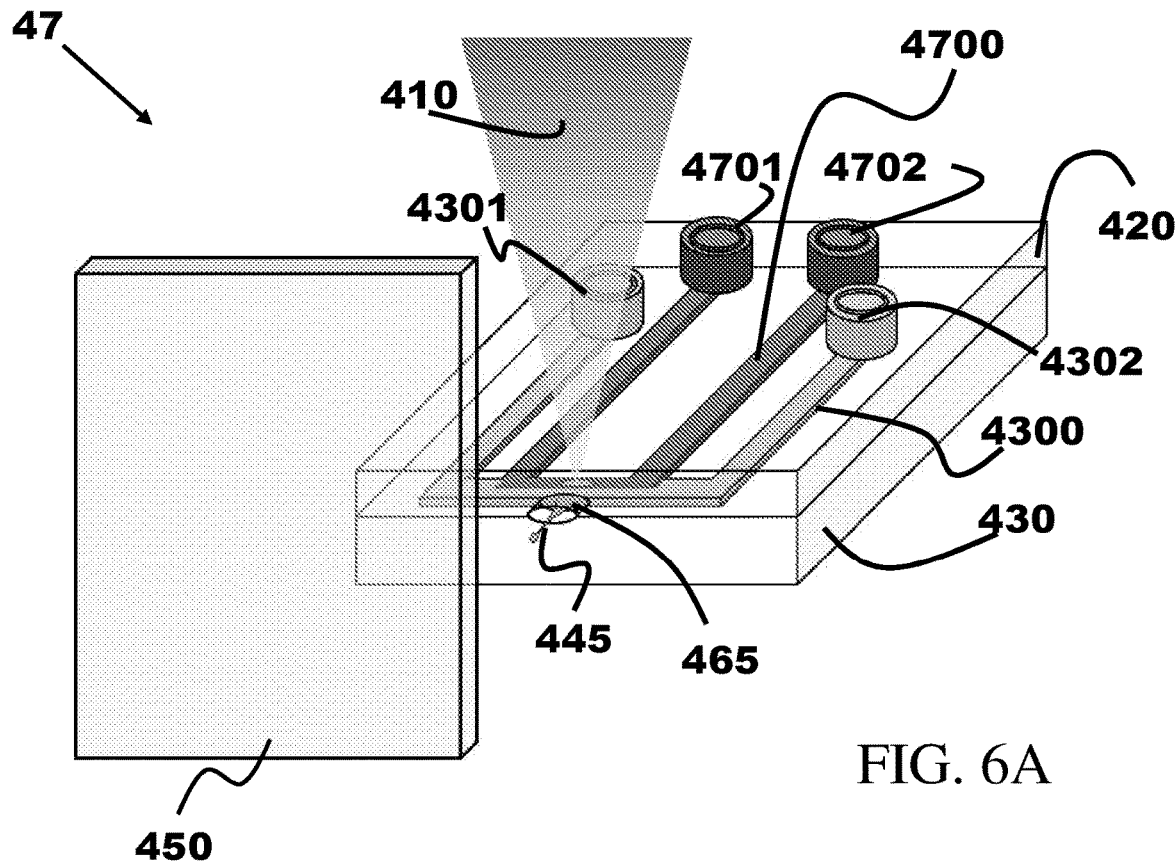
Figure 6B:
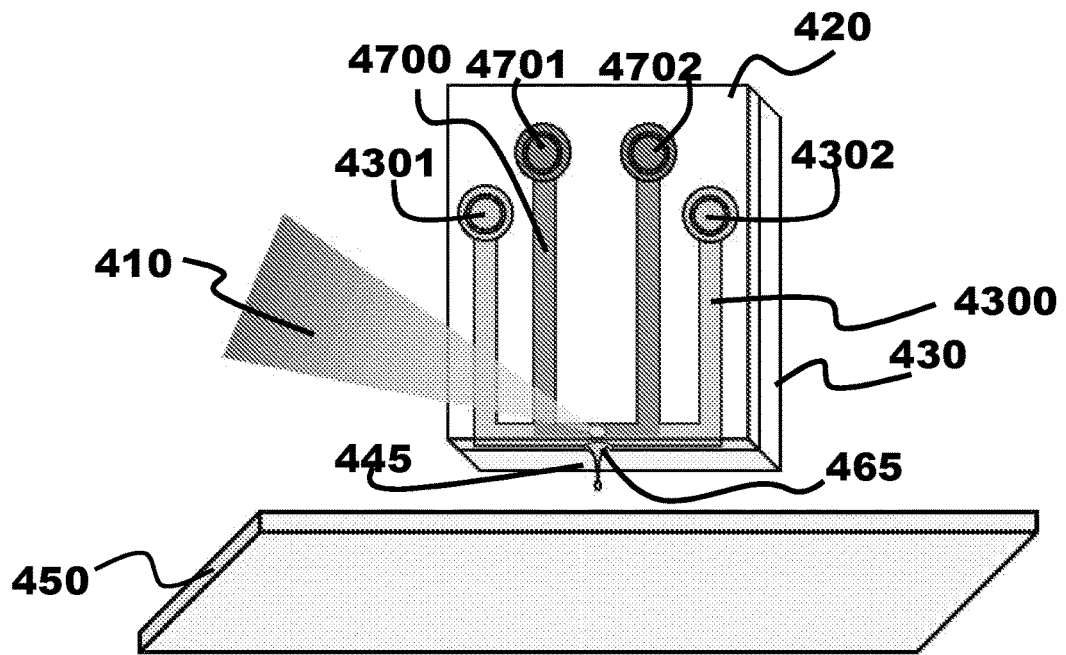

Reference is now made to FIG. 6, which presents schematically bottom (FIG. 6A) and side (FIG. 6B) views of a fourth non-limiting embodiment 47 of the LIFT head of the instant invention. In the embodiment illustrated in FIG. 6, laser output 410 is not coplanar with ink channel 4300 or intermediate layer channel 4700, but rather is at an angle (in preferred embodiments, perpendicular) to the plane of the ink channel. In these embodiments, the three regions of the MFC are not arranged vertically one above the other. Rather, the lower region, which includes orifice 465, is oriented to the side of the upper region through which the laser beam passes, and the middle region, which contains the ink flow and intermediate layer channels. Thus, in the embodiment shown in FIG. 6, the "lower region" is actually more of a conceptual region than a separate physical layer. In the embodiment illustrated in the figure, the inlets and outlets of the channels are located on the same face of the MFC as that through which the laser beam passes, i.e. the ink and intermediate layer materials flow through the upper layer to reach channels 4300 and 4700. The ink jet 445 exits from a side of the MFC that is adjacent to the side through which the laser beam enters the MFC. It is known in the art that the ink jet formed during the LIFT process does not necessarily have to propagate in the same direction as the laser beam; see, for example, "Laser-Generated Liquid Microjets: Correlation between Bubble Dynamics and Liquid Ejection" (Patrascioiu, A.; Fernández-Pradas, J. M.; Palla-Papavlu, A.; Morenza, J. L.; Serra, P. *Microfluid Nanofluid* 16, 2014, 55), and "Time-Resolved Imaging of the Laser Forward Transfer of Liquids" (Duocastella, M.; Fernández-Pradas, J. M.; Morenza, J. L.; Serra, P. *J. Appl. Phys.* 106, 2009, 084907), both of which are hereby incorporated by reference in their entirety. The inlets and outlets may, however, be located on any position of the MFC that is convenient for the specific use to which the LIFT system is being put, and for the optimal overall geometry of the system for that specific use. Alternative geometries such as those in which the inlet and outlet are located on one or more of the sides of the MFC perpendicular to the side through which the laser beam passes are considered by the inventors to be within the scope of the invention.

In the embodiments illustrated in FIGS. 3-6, the MFC printing head comprises a single orifice. Embodiments of the invention in which the printing head comprises a plurality of orifices, each of which is in fluid connection with the ink channel, are considered by the inventors to be within the scope of the invention.

In preferred embodiments such as the ones illustrated in FIGS. 3-6, the fluid connection between the two channels is a few mm in length.

The sizes of the channels are optimized for the particular material being used. In typical embodiments of the invention, the height of each channel is between 20 μm and 1 mm, and its width is between 50 μm and 3 mm. As a general rule, a smaller channel height will result in smaller droplets being ejected as the ink jet, and will require less energy per pulse than a higher channel would need. On the other hand, if the material flowing through the channel is highly viscous, a channel having smaller dimensions will result in a larger pressure drop, especially in the cases of highly viscous inks flowing through the MFC at a high velocity, which can lead to several possible problems, such as clogging of the ink in the channel, leaking of ink from the orifice in the bottom region due to uneven flow, and in severe cases, even breaking of the chip. In addition, flow under these conditions is difficult to generate and control by use of ordinary pumps.

In some embodiments of the invention, the two channels have different interior dimensions. In general, the height of the intermediate layer channel will depend on the details of the particular application in which the LIFT system is being used, while the total width of the two channels will define the total length scale of the LIFT process. For example, in embodiments in which the energy source is a laser, then the optimum height of the intermediate layer channel will be determined by the absorbance of the material that flows through the intermediate layer at the laser output wavelength and the laser output energy at that wavelength, with the height being determined by the optical depth necessary for sufficient energy to be absorbed to provide the vapor bubble that drives the LIFT process.

In some embodiments of the invention, the inlet and outlet of each channel have different dimensions with the ink channel varying from its one end to the other, in order to provide better pressure control at the orifices. In some embodiments of the invention, the inlet and the outlet comprise standard connectors to connect the ink and intermediate layer channels to the conduits that transfer the ink and intermediate layer material to and from the MFC LIFT head.

The LIFT system depicted in FIGS. 3-6 comprises a source of energy (e.g. laser output 410). Intermediate layer channel 4700 comprises an inlet 4701 and an outlet 4702, and ink channel 4300 comprises an inlet 4301 and an outlet 4302. In typical embodiments of the invention, connections between channel inlets and outlets and external tubes are made by standard microfluidic connectors. The external tubes provide a fluid connection between the MFC and at least one pump that creates the flow of ink and the material of the intermediate layer through the channel. Non-limiting examples of the types of pumps that can be used with the MFC head disclosed herein include peristaltic, pressure, and syringe pumps. The required flow rate of the fluids will depend on the required refresh rate, which depends inter alia on the droplet sizes in the ink jet and the desired printing rate. In typical embodiments of the invention, the flow rate is between 1 mm s$^{-1}$ and 1 m s$^{-1}$. In some embodiments of the invention, the volumetric flow rate is less than 0.01 μL s$^{-1}$.

The flow rate can be governed by either volumetric flow rate control or by pressure difference control. In some embodiments of the invention, the stability of the liquid level at the orifice is maintained by having the suction at the exit be greater than the pressure at the inlet. In other non-limiting embodiments of the invention, the liquid level and shape at the orifice are monitored by a closed feedback loop; by measuring the pressure inside the MFC, at the inlet, or at the outlet; or by measuring the shape of the meniscus formed by the ink at the orifice.

Other non-limiting optional components of the LIFT system disclosed herein include an air trap, pressure sensors, pressure regulators, flow-rate sensors, valves, and temperature control apparatus.

The orifice can be of any shape or size appropriate to the desired output of the LIFT system. As non-limiting examples, shape and size of the orifice can be chosen for purposes such as controlling the LIFT process; stabilizing the flow through the MFC; controlling the shape of the meniscus at the orifice; and preventing unwanted ejection of liquid from or introduction of air bubbles into the MFC. In typical embodiments of the invention, the orifice will have either a round or a square shape. In some non-limiting embodiments of the invention, the orifice may have either a trapezoidal or an elliptical shape. In some other non-limiting embodiments of the invention, the orifice has non-uniform boundaries. The diameter of the orifice typically ranges from 100 μm to 1 mm, depending on the viscosity and flow rate of the ink.

In some embodiments of the invention, the orifice is coated or subject to or other surface treatment that will alter the contact angle of the ink droplets being formed. The coating or surface treatment may be of any appropriate type known in the art, and prepared by any appropriate method known in the art.

In typical embodiments of the LIFT system, such as those shown in FIGS. 3-6, the LIFT head faces a substrate 450. The LIFT process is then use to deposit ink 455 on the substrate, as described in detail below.

It is within the scope of the invention to disclose a LIFT method that is based on the use of an MFC LIFT head. In a typical embodiment of the LIFT method disclosed herein, ink flows through ink channel 4300, entering the MFC through inlet 4301 and exiting through outlet 4302. Simultaneously, intermediate layer material, which strongly absorbs the input energy that drives through the process, flows through intermediate layer channel 4700, entering the MFC through inlet 4701 and exiting through outlet 4702. As described above, fluid connection 480 between the two channels enables contact of the two materials; downstream of the fluid connection, the two channels separate in order to enable recycling of the intermediate layer material and of the ink. Because the design of the MFC LIFT head ensures laminar flow of the intermediate material and of the ink, there will be essentially no mixing of the two materials even though there is a the fluid connection between the channels that carry the materials.

Laser output 410 is focused on the intermediate layer channel, preferably in the region of the channel where the fluid connection between the intermediate layer channel and the ink channel is found. The laser light is at least partially absorbed by the material in the intermediate layer channel, thereby causing a transient pressure wave. Without being bound by theory, there are several plausible mechanisms by which the transient pressure wave can be created. For example, if the intermediate layer material absorbs sufficient energy for it to at least partially evaporate, a vapor bubble will be formed that, upon collapse, will cause a transient pressure increase. In another possible mechanism for creation of the transient pressure wave, the absorption of light by the intermediate layer material may be sufficient to heat the intermediate layer material without evaporating it, thereby causing a transient pressure wave as the material expands. In a third possible mechanism, the laser light ablates or partially ablates intermediate layer material, thereby causing the transient pressure wave. Which mechanism or combination of mechanisms is operative in a particular system will depend on details of the system such as the nature of the intermediate layer material, the wavelength and pulse energy of the laser output, and so on.

The pressure wave caused by the absorption of energy in the intermediate layer passes to the ink flowing through the ink layer via the fluid connection connecting the intermediate layer and ink layer channels, causing ink to be forced through orifice 465 toward the receiving substrate 450, thereby creating ink jet 445 that is then deposited (455) on the receiving substrate. In contrast to normal LIFT processes, however, in the instant invention, fresh sample is brought before the laser by the aforementioned flow of intermediate layer material and ink through the MFC rather than by movement of the LIFT head or laser.

The channels in the MFC may be prepared by any method known in the art. In preferred embodiments of the invention, the channels in the MFC are prepared by ablating, molding, mechanical milling, or embossing the thick layer in the desired shape. The lower region is then used to seal the channels.

The wavelength, polarization, and mode distribution of the laser light are restricted only by the requirement that the absorption coefficient for absorption of the laser output by the intermediate layer must be sufficiently high that a single laser pulse is sufficient to at least partially evaporate the ink that absorbs the light in order to create the vapor bubble and eventually the ink jet that exits the MFC via the orifice. In preferred embodiments of the invention, the absorption coefficient of the intermediate layer material at the laser wavelength is at least 1000 $cm^{-1}$.

The system and method of the present invention are thus particularly useful in cases in which the ink itself does not absorb strongly at the laser output wavelength.

For the printing of living cells, a liquid or gel medium is used that has mechanical, biological, and optical properties appropriate to the specific application for which the system is being used. Commercially available bio-inks can be used in the invention herein disclosed. Non-limiting examples of materials from which compatible bio-inks can be made include collagen, gelatin, alginate, gellan gum, polyethylene glycol, and hyaluronic acid. Most of these bio-inks are hydrogels comprising an aqueous solution of polymer and cross-linker. These bio-inks tend to have dynamic viscosities ($\mu t$) between 200 and $10^4$ mPa·s at low shear rates. At higher flow rates, these gels tend to show shear thinning behavior having an approximately power-law relation with flow behavior index n=0 (i.e. $\mu = K\tau^{-1}$, where $\tau$ is the shear rate and K is a constant). The viscosity may be selected to have a value that is appropriate to the particular application or specific biological tissue to which the LIFT printing is being applied.

In preferred embodiments of the invention, the laser pulse duration is ≤10 ns. The use of lasers that produce picosecond or femtosecond pulses are within the scope of the invention. In preferred embodiments of the invention, the laser fluence at the focus is greater than 0.2 J $cm^{-2}$.

In typical embodiments of the invention, the laser light travels through free space, directed as needed by beam steering and focusing elements known in the art such as galvanometers, mirrors, simple lenses, and microscope objectives. In typical embodiments, the laser output is focused to a spot size having a radius of between 1 μm and 1 mm. The spot size will depend on the particular application, as the size of the droplets of ink exiting the head is directly related to the laser spot size.

While embodiments of the invention in which the laser light travels to the MFC via free space are considered by the inventors to be within the scope of the invention, in some preferred embodiments of the invention, the laser energy is transferred to the ink via an optical fiber. Because of the high laser pulse energies used in the LIFT process, in preferred embodiments of the invention in which optical fibers are used to transfer the laser energy to the LIFT head, hollow-core optical fibers or photonic-crystal fibers (PCFs) are used. In some embodiments of the invention, the fiber is inserted into the MFC and immersed in the ink. In some preferred embodiments of the invention in which optical fibers are used to transfer the laser energy to the LIFT head and in which the optical fiber is kept outside of the MFC, collimation of the light at the end of the fiber is done by embedding a focuser at the end of the fiber. Any appropriate type of focuser known in the art can be used. In some embodiments of the invention a scanner or other alignment means is used in addition to the focusing elements.

In some embodiments of the invention, the system comprises a plurality of MFC LIFT printing heads. These embodiments are particularly useful for cases in which different inks are to be applied to the substrate or if a high printing rate is desired. In cases in which inks of different materials are used, the different MFC heads can be designed with different dimensions or architectures optimized for the properties of the ink. As a non-limiting example, the diameters of the ink channels can be set to optimize the flow for materials of different viscosities.

In the embodiments in which multiple printing heads are used, separate lasers can be used for each printing head, or a single laser can be used and its output divided among the heads either physically, for example by using beamsplitters or a plurality of optical fibers, or temporally by alternating the head to which the laser light is sent. As a non-limiting example, in a system with 5 printing heads for which a 10 kHz printing rate is desired, a laser firing at a 50 kHz repetition rate can be used with successive pulses directed to successive heads, or a single laser firing at a 10 kHz repetition rate in which the output is divided physically among the printing heads can be used instead. In some embodiments of the invention in which multiple printing heads are used, the system includes a single reservoir for ink or a single reservoir for intermediate layer material or both. All of the printing heads are connected, either in series or in parallel, to the single reservoir.

The embodiment of the invention illustrated schematically in FIG. 3 shows the MFC LIFT head located above the receiving substrate. Because gravitational effects are not very significant on the length scale of the LIFT process disclosed herein, the MFC LIFT head may be placed in any convenient orientation relative to the receiving substrate, and all possible orientations of the MFC LIFT head relative to the receiving substrate, including but not limited to cases in which the ink jet is expelled horizontally or in which the MFC LIFT head is located below the receiving substrate are considered by the inventors to be within the scope of the invention.

LIFT systems that incorporate the MFC LIFT head described above are also within the scope of the invention. As a non-limiting example of how the LIFT head and receiving substrate may be positioned and oriented, in some embodiments of LIFT systems that incorporate an MFC LIFT head, the position and orientation of at least one of the MFC or the receiving substrate are controlled by placing the component on an XYZ stage. As another non-limiting embodiment of how the LIFT head and receiving substrate may be positioned and oriented, in some other embodiments of LIFT systems that incorporate an MFC LIFT head, at least one of the MFC or the receiving substrate is placed on an XY stage, and the other component is placed on stage or other mount that allows it to move in the Z direction (i.e. controls the distance between that component and the component mounted on the XY stage). The stages or mounts upon which the components are placed are preferably electrically actuated and preferably having a precision of $\pm 1$ μm or better in each direction. In other embodiments The MFC LIFT head is typically placed so that the orifice is between 50 μm and a few mm from the receiving substrate. One of ordinary skill in the art will appreciate that the exact distance between the orifice and the receiving substrate will depend on parameters of the specific application, for example, the specific properties of the ink used and the droplet size and shape required by the application.

In some embodiments of the invention, the LIFT system additionally includes a source of light placed so as to irradiate the receiving substrate and thereby stimulate the secondary gelation or curing of the ink after it has been deposited on the receiving substrate. The light may be of any wavelength suitable to effect activation of the hydrogel, and is typically in the visible or UV range, depending primarily on the cross-linker used. The irradiation of the receiving substrate may be performed continuously during printing, at the end of the process, or, particularly in 3D printing applications, after each layer of ink has been deposited on the receiving substrate.

The upper limit on the printing rate is determined primarily by the laser repetition rate, the maximum flow rate of the ink, and the surface re-initialization time. Printing rates of 1 MHz or more are possible in principle with the LIFT system disclosed herein. In practice, the upper limit on the printing rate is generally set by the viscosity of the ink. LIFT systems that incorporate the MFC head disclosed herein typically have printing rates of ~10 kHz.

The LIFT system disclosed herein is not limited to applications for which high repetition rates are necessary or desirable. Repetition rates of below 100 Hz are quite feasible with the LIFT system, such as bio-printing applications that have typical repetition rates of on the order of 1 Hz are quite feasible with the LIFT system disclosed herein. In fact, the LIFT system disclosed herein is capable of printing even a single drop of ink.

Particularly for biological applications such as printing of biological solutions and the use of cell-based bio-inks, the system additionally includes apparatus for controlling the environment, preferably apparatus that can control at least the temperature, humidity, and $CO_2$ and $O_2$ levels. Typical printing temperatures for biological applications are between 4° C. and 37° C. Any appropriate type of environmental control system known in the art may be used. In addition, in biological applications, the system is preferably placed in a sterile hood that comprises air-flow control, and in preferred embodiments of the system as used in biological applications, the printing head is sterilized prior to use and most preferably during use as well as needed to prevent contamination.

We claim:

1. A Laser-Induced Forward Transfer (LIFT) printing system, comprising:
    an energy source;
    a receiving substrate;
    at least one printing head disposed between said energy source and said receiving substrate, said printing head comprising a microfluidic chip (MFC), said MFC comprising three regions:
        an upper region;
        a middle region comprising:
            at least one ink channel passing through said MFC, said at least one ink channel comprising an ink channel inlet and an ink channel outlet;
            at least one intermediate layer channel passing through said MFC, said at least one intermediate layer channel comprising an intermediate layer channel inlet and an intermediate layer channel outlet; and,
            a fluid connection within said MFC between said at least one ink channel and said at least intermediate layer channel; and,
        a lower region, said lower region comprising an orifice in fluid connection with said ink channel, said orifice oriented such that fluid exiting said orifice will travel toward said receiving substrate;

said at least one ink channel and said at least one intermediate layer channel being disposed at said fluid connection such that said ink channel lies between said intermediate layer channel and said orifice;
an ink reservoir in fluid connection with said ink channel inlet;
an intermediate layer material reservoir in fluid connection with said intermediate layer channel inlet.

2. The LIFT printing system according to claim 1, wherein said energy source comprises at least one laser providing pulsed output.

3. The LIFT printing system according to claim 2, comprising at least one of the following:
focusing means configured to focus said laser output to a spot characterized by a radius of between about 1 µm and about 1 mm; and,
at least one optical fiber disposed so as to transmit said pulsed output from said laser to said printing head.

4. The LIFT printing system according to claim 2, comprising intermediate layer material, wherein said laser is configured to provide output characterized by at least one of the following:
said output is at a wavelength at which said intermediate layer material absorbs and of sufficient energy such that upon irradiation by said output, said intermediate layer material is at least partially evaporated, ablated, or thermally expanded; and,
said output is at a wavelength at which said intermediate layer material absorbs and of sufficient energy such that upon irradiation by said output, said intermediate layer material absorbs sufficient energy such that a transient pressure wave is created within said intermediate layer material.

5. The LIFT printing system according to claim 1, comprising intermediate layer material, wherein said intermediate layer material comprises at least one material selected from the group consisting of dyes, pigments, and nanoparticles.

6. The LIFT printing system according to claim 1, comprising at least one of:
pumping means for pumping ink from said ink reservoir to said ink channel inlet and through said ink channel;
pumping means for pumping intermediate layer material from said intermediate layer reservoir to said intermediate layer channel inlet and through said intermediate layer channel;
pumping means for recirculating ink from said ink reservoir through said ink channel inlet and back to said ink reservoir; and,
pumping means for recirculating intermediate layer material from said intermediate layer reservoir through said intermediate layer channel and back to said intermediate material reservoir.

7. The LIFT printing system according to claim 1, wherein one of the following is true:
at least one of said head and said receiving substrate is mounted on an XYZ stage having a precision of ±1 µm or better in each direction; and,
one of said head and said receiving substrate is mounted on an XY stage having a precision of ±1 µm or better in each direction, and the other component is mounted on a stage or mount configured to move said other component along a Z axis.

8. The LIFT printing system according to claim 1, comprising n printing heads, n>1.

9. The LIFT printing system according to claim 8, wherein said energy source is characterized by at least one of the following:
said energy source is configured to irradiate each of said n printing heads sequentially; and,
said energy source comprises n energy sources, each of which is configured to irradiate one of said n printing heads.

10. A method for Laser-Induced Forward Transfer (LIFT) printing, wherein said method comprises:
obtaining a LIFT printing system comprising:
an energy source;
a receiving substrate; and,
at least one printing head disposed between said energy source and said receiving substrate such that an ink jet created by a pressure transient within said printing head following delivery of a pulse of energy from said energy source to said printing head will exit said printing head toward said receiving substrate, said printing head comprises a microfluidic chip (MFC), said MFC comprising three regions:
an upper region;
a middle region comprising:
at least one ink channel passing through said MFC, said at least one ink channel comprising an ink channel inlet and an ink channel outlet;
at least one intermediate layer channel passing through said MFC, said at least one intermediate layer channel comprising an intermediate layer channel inlet and an intermediate layer channel outlet; and
a fluid connection within said MFC between said at least one ink channel and said at least inter mediate layer channel; and,
a lower region, said lower region comprising an orifice in fluid connection with said ink channel;
said at least one ink channel and said at least one intermediate layer channel being disposed at said fluid connection such that said ink channel lies between said intermediate layer channel and said orifice;
an ink reservoir in fluid connection with said ink channel inlet; and,
an intermediate layer material reservoir in fluid connection with said intermediate layer channel inlet;
flowing ink from said ink reservoir through said at least one ink channel;
flowing intermediate layer material from said intermediate layer reservoir through said at least one intermediate layer channel;
irradiating said intermediate layer material with output of an energy source, said output having sufficient energy at a location at which said intermediate layer material is irradiated to at least partially evaporate said intermediate layer material at said fluid connection, such that upon collapse of a vapor bubble formed upon said irradiation, a transient pressure increase is created, thereby forcing ink out of said orifice; and
receiving said ink forced out of said orifice on at least one predetermined location on a receiving substrate.

11. The method according to claim 10, wherein said step of flowing ink comprises flowing said ink at a flow rate selected from the group consisting of:
a flow rate of between about 1 mm s$^{-1}$ and about 1 m s$^{-1}$; and,
a volumetric flow rate of less than 0.01 µL s$^{-1}$.

12. The method according to claim 10, wherein said step of flowing intermediate layer material comprises flowing said intermediate layer material at a flow rate selected from the group consisting of:
- a flow rate of between about 1 mm s$^{-1}$ and about 1 m s$^{-1}$; and,
- a volumetric flow rate of less than 0.01 μL s$^{-1}$.

13. The method according to claim 10, wherein said step of irradiating comprises irradiating with output of a pulsed laser at a wavelength at which said intermediate material absorbs.

14. The method according to claim 10, wherein said step of irradiating comprises transmitting said pulsed output from said laser to said printing head by means of an optical fiber.

15. The method according to claim 10, wherein said step of flowing ink from said ink reservoir through said at least one ink channel comprises recirculating said ink back into said ink reservoir.

16. The method according to claim 10, wherein said step of flowing intermediate layer material from said intermediate layer material reservoir through said at least one intermediate layer channel comprises recirculating said intermediate layer material back into said intermediate layer material reservoir.

17. The method according to claim 10, comprising a step selected from the following:
- positioning at least one of said head and said receiving substrate on an XYZ stage having a precision of ±1 μm or better in each direction; and,
- positioning one of said head and said receiving substrate on an XY stage having a precision of ±1 μm or better in each direction and other of said head and said receiving substrate on a stage or mount configured to move said other component along a Z axis.

18. The method according to claim 10, wherein said step of flowing comprises flowing said ink through channels in n printing heads, n>1, and said step of irradiating comprises irradiating ink in each of said n printing heads.

19. The method according to claim 18, wherein said step of irradiating comprises at least one step selected from the group consisting of:
- irradiating each of said n printing heads sequentially; and,
- irradiating with the output of n energy sources, each of which is configured to irradiate one of said n printing heads.

20. The method according to claim 10, comprising moving said printing head relative to said substrate during said LIFT printing process.

* * * * *